(12) United States Patent
Gardner

(10) Patent No.: US 10,377,646 B2
(45) Date of Patent: Aug. 13, 2019

(54) ELECTROLYZED WATER COMPOSITION

(71) Applicant: Ozo Innovations LTD, Oxfordshire (GB)

(72) Inventor: Stephen Philip Gardner, Gloucestershire (GB)

(73) Assignee: Ozo Innovations LTD, Oxfordshire (GB)

( * ) Notice: Subject to any disclaimer, the term of this patent is extended or adjusted under 35 U.S.C. 154(b) by 0 days.

(21) Appl. No.: 15/531,855

(22) PCT Filed: Dec. 4, 2015

(86) PCT No.: PCT/GB2015/053717
§ 371 (c)(1),
(2) Date: May 31, 2017

(87) PCT Pub. No.: WO2016/092272
PCT Pub. Date: Jun. 16, 2016

(65) Prior Publication Data
US 2017/0267553 A1    Sep. 21, 2017

(30) Foreign Application Priority Data

Dec. 9, 2014  (GB) .................................. 1421867.1
Oct. 19, 2015  (GB) .................................. 1518472.4
Oct. 19, 2015  (GB) .................................. 1518474.0

(51) Int. Cl.
*A61L 2/18*    (2006.01)
*C02F 1/78*    (2006.01)
(Continued)

(52) U.S. Cl.
CPC ............ *C02F 1/4672* (2013.01); *A23L 3/358* (2013.01); *C02F 1/46104* (2013.01); *C25B 1/13* (2013.01);
(Continued)

(58) Field of Classification Search
CPC ..... C02F 1/4672; C02F 2303/04; C25B 15/08
(Continued)

(56) References Cited

U.S. PATENT DOCUMENTS

2007/0023273 A1    2/2007  Kitaori et al.
2012/0285825 A1    11/2012  Benedetto
(Continued)

FOREIGN PATENT DOCUMENTS

WO    WO-2013/064688 A2    5/2013
WO    WO-2013/064695 A2    5/2013

OTHER PUBLICATIONS

Kurtulan Dogan, M., "International Search Report", prepared for PCT/GB2015/053717, dated Mar. 9, 2016, 4 pages.

*Primary Examiner* — Helen F Heggestad
(74) *Attorney, Agent, or Firm* — Winstead PC

(57) ABSTRACT

The present invention provides a method for producing electrolyzed water composition for use in cleaning and disinfecting of an object. The method comprises preparing an electrolyte solution comprising water, at least one carbonate salt selected from: alkali metal carbonate salts, and at least one chloride salt selected from: alkali metal chloride salts and/or alkali earth metal chloride salts. The method further comprises introducing the aqueous electrolyte solution into an electrolytic cell comprising a plurality of boron-doped diamond electrodes. The method further comprises operating a power supply to apply a predetermined voltage to the electrolyte solution to produce an electrolyzed water composition comprising a plurality of active molecular and ionic species with antimicrobial activity.

8 Claims, 8 Drawing Sheets

(51) Int. Cl.
*C25B 1/13* (2006.01)
*C25B 9/06* (2006.01)
*A23L 3/358* (2006.01)
*C02F 1/461* (2006.01)
*C02F 1/467* (2006.01)

(52) U.S. Cl.
CPC ............ *C25B 9/06* (2013.01); *A23V 2002/00* (2013.01); *A61L 2/183* (2013.01); *C02F 1/78* (2013.01); *C02F 2001/46147* (2013.01); *C02F 2001/46185* (2013.01); *C02F 2201/4618* (2013.01); *C02F 2209/23* (2013.01); *C02F 2303/04* (2013.01); *Y02E 60/366* (2013.01)

(58) Field of Classification Search
USPC .............................. 426/61, 72, 335, 532, 541
See application file for complete search history.

(56) References Cited

U.S. PATENT DOCUMENTS

| | | |
|---|---|---|
| 2013/0032491 A1 | 2/2013 | Nitta et al. |
| 2013/0125316 A1 | 5/2013 | Bhuta et al. |

$T_1$ - 5 Minutes $T_3$ - 40 Minutes $T_0$ - Before $T_2$ - 20 Minutes

UNTREATED - 10 days

REVUS - 10 days

UNTREATED - 10 days

Mix 38 - 10 days

ELECTROLYZED WATER COMPOSITION

FIELD OF THE INVENTION

The present invention relates to an electrolyzed water composition, an apparatus and a method for preparing an electrolyzed water composition, and the use of an electrolyzed water composition for use in disinfecting items within for example the food industry. The present invention also relates to the use of an electrolyzed water composition for the treatment of pathogens, including fungal, bacterial and viral pathogens, within for example the agricultural industry. The present invention also relates to the use of the electrolyzed water compositions for reducing and/or eliminating food-borne pathogens on or in food products, such as for example on or in meat or poultry carcasses.

BACKGROUND

In the food industry, equipment such as for example processing lines and tools, needs to be disinfected in order to minimise the risk of microbial contamination. Microbial contamination can lead to spoilage of food products, reduced shelf life and/or food poisoning of the consumer. As a result, microbial contamination issues cost the food industry billions of pounds a year.

There are a number of conventional anti-microbial agents available for disinfecting hard surfaces, such as for example peracetic acid and sodium hypochlorite. Due to safety concerns, these anti-microbial agents cannot however be used within food preparation and processing environments where there is an increased risk of the anti-microbial agents coming into contact with food products. There is a concern that these anti-microbial agents may on contact with a food product enter the food chain and/or taint the food product.

Conventional cleaning chemicals and disinfectants have also been used within the food industry. However even after long and expensive cleaning cycles, it has been found that the background microbiological levels of the cleaned equipment remains too high and the risk of microbial contamination remains. There is also the concern that these chemicals may taint food products.

Other methods for cleaning equipment involve the use of electrolyzed water compositions. Conventional methods for producing electrolyzed water typically involve the use of electrolyte solutions comprising a solution containing a chlorine ion. When the electrolyte solution is produced through electrolytic oxidation, and by dissolving the chlorine gas in water, hypochlorous acid is generated. The resultant electrolyzed water compositions can be used for disinfecting surfaces, however these compositions contain free accessible chlorine (FAC). The level of chlorine containing salts in the feed stream to an electrolytic cell is selected based on the level of disinfecting required by the chlorine containing active species of the resultant electrolyzed water composition. Use of the conventional electrolyzed water compositions therefore produces, either when prepared or when reacted, a chlorine related smell which is commonly associated with swimming pools. There is therefore a risk that if these electrolyzed water compositions are used within food processing and preparation environments, these compositions may taint the food product produced by the disinfected apparatus. Current EU regulations require that in certain situations, direct food contact disinfecting solutions contain FAC of less than 20 ppm, which is ineffective at killing for example human food pathogens such as *Campylobacter* on chicken carcasses.

*Campylobacter* contamination is known to be the most common cause of food poisoning in the UK, causing up to 280,000 serious food poisonings and up to 200 deaths in the UK every year. *Campylobacter* can be found in poultry, red meat, unpasteurised milk, and untreated water. In particular, *Campylobacter* contamination of chicken is a major food safety problem. About four in five cases of *Campylobacter* poisoning in the UK comes from contaminated poultry. Although *Campylobacter* does not normally grow in food, it is known to spread easily and has a low infective dose. As a result, illness can be caused by the presence of a few bacteria being transferred from uncooked food (such as for example chicken), to ready to eat foods. *Campylobacter* contamination has a significant impact on the UK economy and it is thought to cost the economy about £900 million a year.

A survey of *Campylobacter* in chickens on retail sale was carried out in the UK between May 2007 and September 2008. The survey identified that *Campylobacter* was present in about 65% of the fresh chicken samples. More recent surveys in 2014 and 2015 have put the presence of *Campylobacter* in UK supermarket chickens at up to 80%. The surveys therefore highlighted that there are a number of *Campylobacter*-related challenges in the current food safety system. One of the main priorities of the Food Standards Agency is to reduced food-borne diseases or pathogens, in particular *Campylobacter* in poultry carcasses.

There is a need for a food-safe, non-tainting composition, for example non-tainting disinfecting composition, for use within the food industry which has improved anti-microbial efficacy, for example improved efficacy against food-borne pathogens. There is a need for a food-safe, non-tainting disinfecting composition which provides improved anti-microbial efficacy and requires a shorter and/or less expensive cleaning cycle. There is a need for a food-safe, non-tainting disinfecting composition which can be used to disinfect food processing lines and equipment in situ. There is a need for a food-safe, non-tainting, disinfecting composition which can be used during and/or between food processing. Standard electrolysed water solutions containing hypochlorous acid cannot be used, partly due to regulations limiting the amount of free accessible chlorine (FAC) in solutions used in food contact applications to below 20 ppm, a level at which it is ineffective, and partly due to its noticeable chlorine smell. There is a need for a food-safe, non-tainting composition which has reduced associated cost implications and/or environmental implications.

There are a number of plant pathogens such as downy mildew, powdery mildew, late onset blight (*Phytopthora*), *Bortrytis* and stem *Bortrytis* which present serious issues to farmers and growers. The plant pathogens may significantly reduce the yield and quality within a wide range of food or flower crops. In some cases, the plant pathogens may destroy up to 100% of viable crops resulting in significant financial losses. These pathogens are often highly selective and affect a very specific food or flower crop. The pathogens are also often very difficult to control in any systemic fashion. The pathogens can continue to spread throughout a crop even with regular spraying with conventional chemical pesticides.

A number of agricultural chemical controls which are currently used to protect crops against plant pathogens are highly toxic to humans. As a result, the grower or farmer must use additional protective equipment and/or wear expensive protective clothing and breathing apparatus. Furthermore, the chemicals may not be used beyond a certain time point in the growing season prior to harvest in order to minimise the risk of chemical residues being present on or in the crops at harvest. The use of these chemicals also has associated environmental implications. The current agricultural controls have come under severe regulatory restriction. Effective disease management options must also be economical. The cost of managing the disease must be less than the value of the crops to be harvested.

There is therefore a need for a biocidal composition with improved efficiency in protecting crops against plant pathogens, lower associated energy and cost implications, and/or reduced environmental and health implications. There is also a need for a method of treating agricultural crops which does not require any additional treatment apparatus.

SUMMARY OF THE INVENTION

According to a first aspect of the present invention, there is provided a method for producing an electrolyzed water composition for use in disinfecting an area, the method comprising:
  preparing an electrolyte solution comprising water, at least one carbonate salt selected from anhydrous alkali metal carbonate salts and at least one alkali metal chloride salt and/or alkali earth metal chloride salt;
  introducing the aqueous electrolyte solution into an electrolytic cell comprising a plurality of boron-doped diamond electrodes; and
  operating a power supply to apply a predetermined voltage to the electrolyte solution within the electrolytic cell to produce an electrolyzed water composition comprising a plurality of active molecular and ionic species having anti-microbial properties.

The electrolyte solution may be introduced into the electrolytic cell in a continuous or batch process manner.

Preferably the at least one chloride salt is sodium chloride.

Preferably the at least one carbonate salt is anhydrous sodium carbonate.

The total salt concentration of carbonate salts and chloride salts within the aqueous electrolyte solution is preferably within the range of between about 0.1 g/l and about 200 g/l. Preferably, the total salt concentration of carbonate salts and chloride salts within the aqueous solution is in the range of between 1 g/l and 80 g/l, more preferably between 5 g/l and 50 g/l, for example in the range of 2.5 g/l and 10.5 g/l.

The ratio of carbonate salt(s) to chloride salt(s) by weight within the aqueous electrolyte solution is preferably in the range of between about 0.5:1 to about 2.0:1, more preferably in the range of between about 1:1 to about 1.5:1, for example about 1.15:1.

The electrolyte solution can optionally include one or more additional salts to enhance the biocidal properties and/or cleaning properties of the resultant electrolyzed water composition.

The predetermined voltage is preferably in the range of between about 1 and 1000 volts DC, preferably in the range of between 48 to 96 volts DC.

The power supply preferably has a current in the range of between about 1 and 1000 ampere, preferably at about 24 ampere.

According to a second aspect, the present invention provides an electrolyzed water composition obtainable by a method as described herein.

According to a further aspect, the present invention provides an electrolyzed water composition obtained by a method as described herein.

The plurality of active molecular and ionic species within the electrolyzed water composition may comprise dissolved $O_3$ in a concentration between about 0.1 and 750 ppm. The electrolyzed water composition preferably comprises dissolved $O_3$ in a concentration between 10 and 500 ppm, more preferably in a concentration between 50 and 300 ppm. The electrolyzed water composition is preferably substantially chlorine-free. The term "substantially chlorine-free" is used herein to refer to a composition comprising less than 0.5 ppm FAC, preferably less than 0.1 ppm FAC, more preferably less than 0.01 ppm FAC, for example 0 ppm FAC.

According to a further aspect, the present invention provides the use of an electrolyzed water composition as herein described as an antimicrobial agent. The electrolyzed water composition may have antibacterial properties.

The compositions of the present invention may be used to disinfect an area. The term "area" is used herein to refer to surfaces, including hard surfaces, substrates, objects, air, and/or food items.

According to a further aspect, the present invention provides a method for disinfecting an area, comprising applying an electrolyzed water composition as herein described.

According to a further aspect, the present invention provides an applicator for disinfecting equipment, in which the applicator comprises a reservoir comprising an electrolyzed water composition as herein described, and a nozzle in fluid communication with the reservoir. The applicator may comprise a reservoir which is arranged in use to be connected to a spraying device or to equipment, such as for example processing lines, within the environment to be disinfected.

The applicator may for example be selected from one or more of: a nebuliser, a fogging mist applicator, a jet spray applicator, a spray applicator, or a wash system, or any combination thereof.

According to a further aspect, the present invention provides an apparatus for producing electrolyzed water composition for use as a disinfectant, the apparatus comprising:
  a reservoir comprising an electrolyte solution comprising water, at least one carbonate salt selected from: anhydrous alkali metal carbonates, and at least one chloride salt selected from: alkali metal chloride salts and/or alkali earth metal chloride salts;
  an electrolytic cell in fluid communication with the reservoir to receive a feed stream comprising the aqueous electrolyte solution; and
  a plurality of boron-doped diamond electrodes located within the electrolytic cell and arranged in use to be connected to a power supply.

The electrolytic cell preferably comprises at least one outlet through which the electrolysed water composition exits the electrolytic cell.

The system may further comprise one or more flow regulators arranged in use to adjust the flow of the electrolyte feed stream between the reservoir and the cell.

The system may further comprise a heater arranged in use to adjust the temperature of the flow of the electrolyte feed stream and/or the electrolyte solution within the cell.

The system may further comprise a control system arranged in use to control the flow rate of the electrolyte feed stream as required, such as for example by controlling the flow regulator(s).

The system may comprise a control system arranged in use to control the power supply to the electrodes.

The system may comprise a control system arranged in use to control the temperature of the electrolyte solution.

Control of the temperature of the electrolyte solution, the flow rate of the electrolyte solution feed stream, and the power supply to the electrodes may be provided by a single control system. Alternatively, these factors may be controlled by separate control systems.

According to a further aspect, the present invention, there is provided a method for producing an electrolyzed water composition for use in the treatment of plant pathogens, the method comprising:
preparing an electrolyte solution comprising water, at least one anhydrous alkali metal carbonate salt, and at least one chloride salt selected from: alkali metal chloride salts and/or alkali earth metal chloride salts;
introducing the aqueous electrolyte solution into an electrolytic cell comprising a plurality of boron-doped diamond electrodes; and
operating a power supply to apply a predetermined voltage to the electrolyte solution within the electrolytic cell to produce an electrolyzed water composition comprising a plurality of active molecular and ionic species having anti-microbial properties,
in which the salts of the electrolyte are selected such that the dissolved $O_3$ concentration is in the range of from 1 to 1000 ppm.

Preferably, the electrolyte solution comprises water, at least one anhydrous alkali metal carbonate salt, and at least one chloride salt selected from: alkali metal chloride salts.

Preferably, the salts of the electrolyte are selected such that the electrolyzed water biocidal composition for use in the treatment of plant pathogens comprises a free accessible chlorine (FAC) concentration in the range of from 0 to 1000 ppm. The electrolyte solution may be introduced into the electrolytic cell in a continuous or batch process manner.

Preferably the at least one chloride salt is potassium chloride or sodium chloride.

Preferably the at least one carbonate salt is anhydrous potassium carbonate or anhydrous sodium carbonate.

The total salt concentration of carbonate salts and chloride salts within the aqueous electrolyte solution is preferably within the range of between about 0.1 g/l and 400 g/l. Preferably, the total salt concentration of carbonate salts and chloride salts within the aqueous solution is in the range of between 0.1 g/l and about 400 g/l, more preferably between 0.5 g/l and 80 g/l, especially preferably between 1.0 g/l and 50 g/l, for example in the range of 1.0 g/l and 5.5 g/l.

The ratio of carbonate salt(s) to chloride salt(s) by weight within the aqueous electrolyte solution is preferably in the range of between about 0.5:1 to about 2.0:1, more preferably in the range of between about 1:1 to about 1.5:1, for example about 1.15:1.

The electrolyte solution can optionally include one or more additional salts to enhance the biocidal properties, in particular the pathogenic activity, of the resultant electrolyzed water composition.

The predetermined voltage is preferably in the range of between about 1 and 1000 volts DC, preferably in the range of between 48 to 96 volts DC.

The power supply preferably has a current in the range of between about 1 and 1000 ampere, preferably at about 24 ampere.

According to a still further aspect, the present invention provides an electrolyzed water composition for use in the reduction and/or elimination of plant pathogens obtainable by a method as described herein.

According to a still further aspect, the present invention provides an electrolyzed water composition for use in the reduction and/or elimination of plant pathogens obtained by a method as described herein.

The plurality of active molecular and ionic species within the electrolyzed water composition for use in the reduction and/or elimination of plant pathogens may comprise dissolved $O_3$ in a concentration between about 1 and 1000 ppm. The electrolyzed water composition for use in the reduction and/or elimination of plant pathogens preferably comprises dissolved $O_3$ in a concentration between 10 and 500 ppm, more preferably in a concentration between 50 and 300 ppm.

The composition can be varied in terms of its composition and degree of overpotential by carrying the concentrations of the salts and by carrying the current applied to the solution. In this way, specific electrolyzed water compositions for use in the reduction and/or elimination of plant pathogens can be created for treating certain microbes or pathogens, including live organisms such as spores and biofilms. The concentrations and overpotential can be varied so as to achieve the required mix between antimicrobial properties, cleaning properties and delivery mechanisms.

According to a further aspect, the present invention provides the use of an electrolyzed water composition as herein described for use in the reduction and/or elimination of plant pathogens as an anti-pathogenic composition.

The compositions of the present invention may be used to reduce and/or eliminate plant pathogens, including for example fungal pathogens and/or bacterial pathogens and/or viral pathogens.

According to a further aspect, the present invention provides a method for reducing and/or eliminating pathogens, in particular plant pathogens, comprising applying an electrolyzed water composition as herein described for use in the treatment of plant pathogen to an area, for example a plant crop or an area containing a plant crop, affected with pathogens.

According to a further aspect, the present invention provides an applicator for reducing and/or eliminating pathogens, in particular plant pathogens, in which the applicator comprises a reservoir comprising an electrolyzed water composition as herein described for use in the reduction and/or elimination of plant pathogens, and an outlet in fluid communication with the reservoir. The outlet may for example be a nozzle. The applicator may comprise a reservoir which is arranged in use to be connected to a spraying device, a fogging mist device or to equipment, such as for example processing lines or wash systems within the environment to be treated.

The applicator may for example be selected from one or more of: a nebuliser, a fogging mist applicator, a jet spray applicator, a spray applicator, or an irrigation system, or any combination thereof.

According to a further aspect, the present invention provides an apparatus for producing electrolyzed water composition for use in reducing and/or eliminating pathogens, in particular plant pathogens, the apparatus comprising:
a reservoir comprising an electrolyte solution comprising water, at least one anhydrous alkali metal carbonate salt, and at least one chloride salt selected from: alkali metal chloride salts and/or alkali earth metal chloride salts;
an electrolytic cell in fluid communication with the reservoir to receive a feed stream comprising the aqueous electrolyte solution; and
a plurality of boron-doped diamond located within the electrolytic cell and arranged in use to be connected to a power supply.

Preferably, the electrolyte solution comprises water, at least one anhydrous alkali metal carbonate salt, and at least one chloride salt selected from: alkali metal chloride salts.

The electrolytic cell preferably comprises at least one outlet through which the electrolysed water composition for use in the reduction and/or elimination of plant pathogens exits the electrolytic cell.

The system may further comprise one or more flow regulators arranged in use to adjust the flow of the electrolyte feed stream between the reservoir and the cell.

The system may further comprise a heater arranged in use to adjust the temperature of the flow of the electrolyte feed stream and/or the electrolyte solution within the cell.

The system may further comprise a control system arranged in use to control the flow rate of the electrolyte feed stream as required, such as for example by controlling the flow regulator(s).

The system may comprise a control system arranged in use to control the power supply to the electrodes.

The system may comprise a control system arranged in use to control the temperature of the electrolyte solution.

Control of the temperature of the electrolyte solution, the flow rate of the electrolyte solution feed stream, and the power supply to the electrodes may be provided by a single control system. Alternatively, these factors may be controlled by separate control systems.

According to a further aspect, there is provided an electrolyte solution comprising at least one anhydrous alkali metal carbonate salt, and at least one chloride salt selected from: alkali metal chloride salts and/or alkali earth metal chloride salts. The electrolyte solution preferably comprises: at least one carbonate salt selected from anhydrous potassium carbonate and/or anhydrous sodium carbonate; and at least one chloride salt selected from potassium chloride and/or sodium chloride. Preferably, the electrolyte solution comprises anhydrous sodium carbonate and sodium chloride.

According to a further aspect of the present invention, there is provided a method for producing an electrolyzed water composition for use in reducing and/or eliminating food-borne pathogens on or in food substrates, the method comprising:

preparing an electrolyte solution comprising water, at least one anhydrous alkali metal carbonate salt and at least one chloride salt selected from: alkali metal chloride salts and/or alkali earth metal chloride salts;

introducing the aqueous electrolyte solution into an electrolytic cell comprising a plurality of boron-doped diamond electrodes; and operating a power supply to apply a predetermined voltage to the electrolyte solution within the electrolytic cell to produce an electrolyzed water composition comprising dissolved ozone ($O_3$) having anti-microbial properties.

Preferably, the electrolyte solution comprises water, at least one anhydrous alkali metal carbonate salt, and at least one chloride salt selected from: alkali metal chloride salts.

The electrolyte solution may be introduced into the electrolytic cell in a continuous or batch process manner.

Preferably the at least one chloride salt is sodium chloride or potassium chloride, or a combination thereof. More preferably, the at least one chloride salt is sodium chloride.

Preferably the at least one carbonate salt is anhydrous sodium carbonate or anhydrous potassium carbonate, or a combination thereof. More preferably, the at least one carbonate salt is anhydrous sodium carbonate.

The total salt concentration of carbonate salts and chloride salts within the aqueous electrolyte solution is preferably within the range of between about 0.1 g/l and about 400 g/l. For example, the aqueous electrolyte solution preferably comprises 56 g anhydrous sodium carbonate, 48 g sodium chloride in 10 l water. Preferably, the total salt concentration of carbonate salts and chloride salts within the aqueous solution is in the range of between 1 g/l and 80 g/l, more preferably between 5 g/l and 50 g/l, for example in the range of 5.4 g/l and 15.6 g/l.

The ratio of carbonate salt(s) to chloride salt(s) by weight within the aqueous electrolyte solution is preferably in the range of between about 0.5:1 to about 2.0:1, more preferably in the range of between about 1:1 to about 1.5:1, for example about 1.15:1.

The electrolyte solution can optionally include one or more additional salts to enhance the anti-pathogenic properties of the resultant electrolyzed water composition against food borne pathogens.

The predetermined voltage is preferably in the range of between about 1 and 1000 volts DC, preferably in the range of between 48 to 96 volts DC.

The power supply preferably has a current in the range of between about 1 and 1000 ampere, preferably at about 24 ampere.

According to a further aspect, the present invention provides an electrolyzed water composition obtainable by a method as described herein for use in reducing and/or eliminating food-borne pathogens on or in food substrates.

According to a further aspect, the present invention provides an electrolyzed water composition obtained by a method as described herein for use in reducing and/or eliminating food-borne pathogens on or in food substrates. For example, the electrolyzed water composition may be used for reducing and/or eliminating *Campylobacter* on food carcasses, in particular on poultry carcasses, such as for example chicken carcasses.

The electrolyzed water composition for use in reducing and/or eliminating food-borne pathogens on or in food substrates may comprise dissolved $O_3$ in a concentration between about 0.1 and 800 ppm, preferably between 1 ppm and 750 ppm. The electrolyzed water composition for use in reducing and/or eliminating food-borne pathogens on or in food substrates preferably comprises dissolved $O_3$ in a concentration between 10 and 500 ppm, more preferably in a concentration between 50 and 300 ppm.

The electrolyzed water composition for use in reducing and/or eliminating food-borne pathogens on or in food substrates is preferably substantially chlorine-free. The term "substantially chlorine-free" is used herein to refer to a composition comprising less than 20 ppm, preferably less than 5 ppm, more preferably less than 0.5 ppm FAC, even more preferably less than 0.1 ppm FAC, especially preferably less than 0.01 ppm FAC, for example 0 ppm FAC.

According to a further aspect, the present invention provides the use of an electrolyzed water composition as herein described for reducing and/or eliminating food-borne pathogens on or in food substrates.

According to a further aspect, the present invention provides a method for reducing and/or eliminating food borne pathogens on and/or in a food substrate comprising applying an electrolyzed water composition as herein described for use in reducing and/or eliminating food-borne pathogens on or in food substrates to a food substrate.

The compositions of the present invention may be applied to the food substrate by any suitable means. The food substrate may, for example, be coated with or immersed within a tank or reservoir containing an electrolyzed water composition of the present invention. The electrolyzed water composition may be maintained at a predetermined temperature for receiving the food substrate. The efficacy of the electrolyzed water composition may be improved by maintaining the composition at a predetermined temperature. The time period over which the pathogen levels are reduced (or eliminated) to an acceptable predetermined level may be reduced by maintaining the electrolyzed water composition at a predetermined level. For example, the electrolyzed water composition may be maintained at room temperature. Alternatively, the electrolyzed water composition may be heated to a temperature of between about 40° C. and 50° C.

The composition of the present invention may be applied by itself or as part of a treatment regime. For example, the composition of the present invention may be applied as a pre-treatment or a post-treatment before or after application of one or more conventional treatments, such as for example Sonosteam or liquid nitrogen. The composition of the present invention may be applied concurrently or in conjunction with one or more conventional treatments.

The food substrate may be contacted with the electrolyzed water composition (for example immersed within a tank comprising the electrolyzed water composition) of the present invention for a predetermined period of time. For example, the food substrate may be contacted with or immersed within the electrolyzed water composition for at least 5 seconds, preferably at least 15 seconds, for example at least 20 seconds. The tank may receive a plurality of food substrates, either simultaneously or sequentially. The efficacy of the electrolyzed water composition may be improved by maintaining the composition at a predetermined level of active species by continual or periodic electrolysis.

According to a further aspect, the present invention provides an applicator for disinfecting equipment, in which the applicator comprises a reservoir comprising an electrolyzed water composition as herein described, and a nozzle in fluid communication with the reservoir. The applicator may comprise a reservoir which is arranged in use to be connected to a spraying device or to equipment for applying the electrolyzed water composition to the food substrate.

The applicator may for example be selected from one or more of: a nebuliser, a fogging mist applicator, a jet spray applicator, a spray applicator, or a wash system, or any combination thereof.

According to a further aspect, the present invention provides an apparatus for producing electrolyzed water composition for use in reducing and/or eliminating food borne pathogens on or in a food substrate, the apparatus comprising:
a reservoir comprising an electrolyte solution comprising water, at least one anhydrous alkali metal carbonate salt and at least one chloride salt selected from: alkali metal chloride salts and/or alkali earth metal chloride salts;
an electrolytic cell in fluid communication with the reservoir to receive a feed stream comprising the aqueous electrolyte solution; and
a plurality of boron-doped diamond electrode located within the electrolytic cell and arranged in use to be connected to a power supply.

Preferably, the electrolyte solution comprises water, at least one anhydrous alkali metal carbonate salt, and at least one chloride salt selected from: alkali metal chloride salts.

The electrolytic cell preferably comprises at least one outlet through which the electrolyzed water composition exits the electrolytic cell.

The system may further comprise one or more flow regulators arranged in use to adjust the flow of the electrolyte feed stream between the reservoir and the cell.

The system may further comprise a heater arranged in use to adjust the temperature of the flow of the electrolyte feed stream and/or the electrolyte solution within the cell.

The system may further comprise a control system arranged in use to control the flow rate of the electrolyte feed stream as required, such as for example by controlling the flow regulator(s).

The system may comprise a control system arranged in use to control the power supply to the electrodes.

The system may comprise a control system arranged in use to control the temperature of the electrolyte solution.

Control of the temperature of the electrolyte solution, the flow rate of the electrolyte solution feed stream, and the power supply to the electrodes may be provided by a single control system. Alternatively, these factors may be controlled by separate control systems.

Compositions of the present invention have significant anti-microbial properties whilst being substantially chlorine-free.

BRIEF DESCRIPTION OF FIGURES

Embodiments of the invention will now be described, by way of example, with reference to the following figures:

FIG. 2A is an image at a time interval of 30 seconds after application. FIG. 2B is an image at a time interval of 10 minutes after application;

DETAILED DESCRIPTION

Example 1—Electrolyzed Water Composition

Figure 1B:
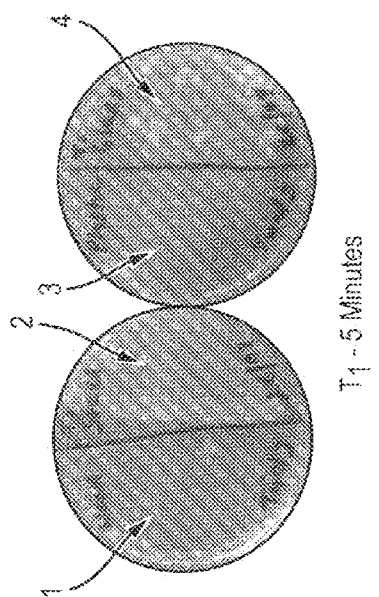
FIGS. 1A to 1D are photographic images illustrating the *E. coli* elimination efficacy of an electrolyzed water composition according to a first embodiment of the present invention applied using a fogging technique to four different substrates (wood, steel, plastic, and glass) as a factor of time after application of the composition.

An electrolyte solution comprising 16 g anhydrous sodium carbonate ($Na_2CO_3$) and 14 g sodium chloride (NaCl) in 5 l of water was prepared. The electrolyte solution is stored within a reservoir chamber in fluid communication with an electrolytic cell.

A feed stream comprising the electrolyte solution was introduced into the electrolytic cell. The feed stream can optionally include one or more additional salts to enhance the disinfectant properties of the resultant electrolyzed water composition. The electrolytic cell is a non-membrane electrolytic cell. The electrolytic cell comprises a casing, a plurality of boron doped diamond electrodes (BDEs) located within the cell, and metal 'contact plates' used for transmitting charge across the electrolyte solution.

The BDEs are sheet-like components and are provided in a stack of between 3 and 10 sheets. Each sheet is located at a fixed distance away from an adjacent sheet. The distance between adjacent sheets of BDEs provides a cell gap, which is preferably less than 5 mm, for example between approximately 2 and 3 mm. The BDEs are provided in a plastic frame. The BDEs transmit charge across the electrolyte solution, inducing a strong dipole and creating positively and negatively charged radicals on alternate surfaces of the diamonds.

The electrolyte solution may be introduced into the electrolytic cell in any suitable manner so as to produce electrolyzed water composition in a continuous process or in a batch process. In the continuous process, the electrolyte solution may be introduced at a suitable flow rate, such as for example at a flow rate in the range of from 0.1 to 100 l/min, for example in the range of from 3 to 5 l/min. In the batch process, the electrolyte solution may have a flow rate of approximately 16 l/min.

A power supply was operated to apply a voltage in the range of between 1 and 1000 Volt D.C. and a current within the range of from 1-1000 ampere to the electrolyte solution. The over-potential provided between the electrodes shifts the equilibrium within the electrolyte solution such that a range of 'active species' ions and molecules are produced and remain within the electrolyzed water for a significant amount of time. For example, the half life of the active species within the electrolyzed water composition is preferably at least a number of minutes, more preferably at least ten minutes, especially preferably at least 30 minutes, for example about 45 minutes.

The electrolytic cell preferably comprises an outlet through which the electrolyzed water composition exits the cell. The resulting electrolyzed water composition comprises a range of active molecular and ionic species which have anti-microbial properties. The electrolyzed water composition preferably also has detergent properties. The electrolyzed water composition preferably comprises surfactant species.

The active molecular and ionic species include dissolved ozone $O_3$ and one or more of: hydrogen peroxide $H_2O_2$, hydroxyl ions $OH^-$ and/or hydronium ions $OH_3^+$. The electrolyzed water composition according to this embodiment comprises dissolved ozone at a level of approximately 300 ppm. This level of dissolved ozone is approximately 100 times greater than the level which can be achieved by injecting gaseous ozone into water. As a result, the electrolyzed water composition of the present invention has an increased anti-microbial efficacy compared to water which has been injected with gaseous ozone. The electrolyzed water composition may be used as an antimicrobial agent, including as an antibacterial agent, antifungal agent, antiviral agent and/or antiparasitic agent, or any combination thereof.

Although the electrolyzed water composition of the present invention contains dissolved ozone at a level of approximately 300 ppm, it is to be understood that the electrolyzed water composition of the present invention may comprise any suitable level of dissolved ozone, preferably within the range of between 0.1 and 1000 ppm, for example within the range of 0.1 ppm and 750 ppm.

Conventional electrolyzed water compositions based on chloride electrolytes generate free accessible chlorine (FAC). Use of the conventional compositions therefore produces, either when prepared or when reacted, a smell which is associated with swimming pools. There is a risk that disinfected equipment within a food processing environment may produce food products which have become tainted with this chlorine associated smell. In contrast, the electrolyzed water composition of the present invention is substantially free of free accessible chlorine (FAC). In the embodiment used in the example, the composition of Example 1 comprises <0.1 ppm FAC both when produced, and when reacted. The compositions of the present invention may therefore be used to clean and disinfect processing lines and equipment without producing a smell associated with a swimming pool and with a significantly reduced risk of tainting the food product. The electrolyzed water compositions of the present invention retain potent anti-microbial properties even though the compositions have low FAC.

TABLE 1

| EN1276 Test results | | | |
|---|---|---|---|
| Test Organism | $Log_{10}$ initial count | Contact Time | $Log_{10}$ Reduction Achieved Dirty Conditions |
| E. coli | >8 | 1 minute | >8 |
| | | 5 minutes | >8 |

Example 2

With reference to Table 1, the electrolysed water composition of Example 1 was applied using an EN1276 test. EN1276 test is the European standard test method to formally evaluate the bactericidal activity of a disinfectant. To meet the requirements of EN 1276 at least a 5 $Log_{10}$, reduction in test bacteria within 5 minutes is required.

The test method involved mixing 1 ml of the test bacteria, in this instance *E. coli*, with 1 ml of interfering substance, in this case 0.3% w/v albumin (simulating dirty conditions), and then adding 8 ml of the electrolysed water composition. After the required contact time, 0.1 ml was removed and added to 8.9 ml of the neutralizer (sterile water) and 1 ml of sterile distilled water. Following a 5 minute neutralization period, 1 ml was plated onto LB Agar to detect surviving test bacteria.

As shown in Table 1, when tested in accordance with EN 1276, the electrolysed water composition achieved >8 $log_{10}$ reduction at 1 and 5 minutes at room temperature under dirty conditions for *E. coli*. The result demonstrates that the electrolysed water composition has high bactericidal activity against *E. coli* and fulfils the requirement of EN1276.

The present invention provides an electrolyzed water composition providing improved anti-microbial activity, for example improved anti-bacterial activity. Although the present invention demonstrates the effectiveness of the electrolyzed water composition with respect to *E. coli*, it is to be understood that the compositions of the present invention are effective against other microbial strains and are not limited to *E. coli*. elimination.

The electrolyzed water composition of the present invention preferably achieves 100% microbial, for example bacterial, elimination within 1 minute of exposure to the composition. The electrolyzed water composition of the present invention preferably achieves 100% microbial, for example bacterial, elimination within 5 minutes, more preferably within 3 minutes, for example within 1 minute, of exposure to the composition. The electrolyzed water composition of the present invention preferably achieves at least 80%, more preferably at least 90%, especially preferably at least 95%, for example at least 99.999% (5 log order) microbial, for example bacterial, elimination within 5 minutes, more preferably within 1 minutes, of exposure to the composition by washing.

Example 3—*E. coli* Elimination Tests using Dry Fogging

With reference to FIGS. 1A-1D, the electrolyzed water composition of Example 1 was applied at a low dosage using a dry fogging method to four different substrates contaminated with *E. coli*: Wood 1, Steel 2, Plastic 3 and Glass 4. It is however to be understood that the composition may be used to disinfect any suitable substrate, and is not limited to use for disinfecting the exemplified substrates.

The electrolyzed water composition was applied using a pulsFOG Rapid Fogger, fitted with a W03 nozzle (herein referred to as a fogging mist applicator). The fogging mist applicator's output rate was approximately 4.5 L/hour, using 2 bar of pressure from a separate air compressor. The output droplet size of the electrolyzed water composition was around 10 to 15 microns.

The fogging mist applicator was located at one end of a shipping container and the four substrates were located adjacent the opposing surface of the shipping container out of direct line of the spray, giving a separation of approximately 6 m.

Although this embodiment illustrates the use of a specific fogging mist applicator it is to be understood that the fogging composition may be applied by any suitable applicator or application method at any suitable output rate using any suitable pressure and producing any suitable output droplet size. The applicator or application method may be located at any suitable distance away from the substrate. For example, the electrolyzed water composition may be contained within a reservoir which is adapted to releasably engaged to equipment for disinfecting, such as for example food processing lines.

Figure 1D:
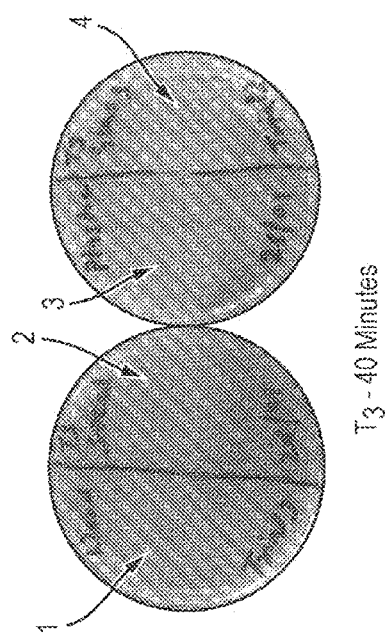
Figure 1A:
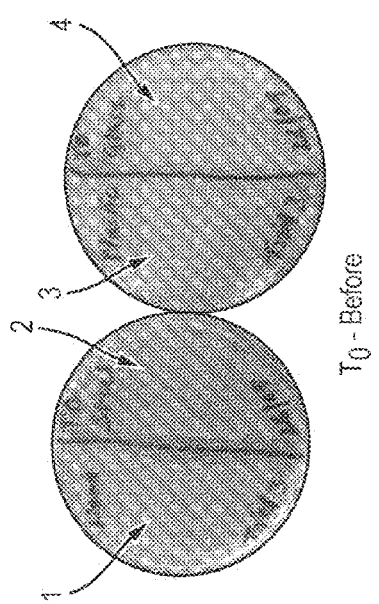
Figure 1C:
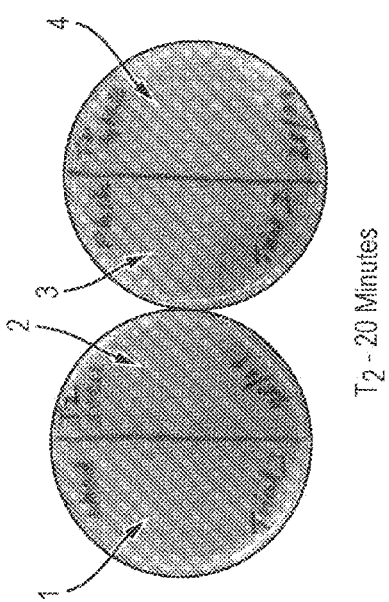

FIG. 1A is a photographic image illustrating the amount of *E. coli* present on each substrate prior ($T_0$) to exposure using the dry fogging method to a low dosage of the electrolyzed water composition of Example 1. The amount of *E. coli* present on each substrate at time intervals $T_1$ (5 minutes); $T_2$ (20 minutes); and $T_3$ (40 minutes) are shown in FIGS. 1B, 1C and 1D respectively.

The presence of *E. coli* is illustrated by white sections/markings on the substrate. The areas where the *E. coli* has been killed by the composition are clear and colourless (no white markings).

As shown in FIG. 1B, the composition of the present invention even at a low dosage provides a 5 log order kill (99.999%) *E. coli* elimination on the plastic substrate after 5 minutes ($T_1$) of fog exposure. It can be seen that the plastic substrate is colourless and clear over the entire surface area.

A high kill rate is also achieved on the wood and glass substrates after 5 minutes of fog exposure to a low dosage of the electrolyzed water composition. It can be seen from FIG. 1B that a few isolated white spots remain on the surface of the wood and glass substrates. It can also be seen that there remains a high *E. coli* presence on the steel substrate after 5 minutes of fog exposure. A white region extends across the majority of the surface of the steel substrate. There is no significant difference between the amount of *E. coli* present on the steel substrate at time $T_0$ and time $T_1$.

Figure 10:
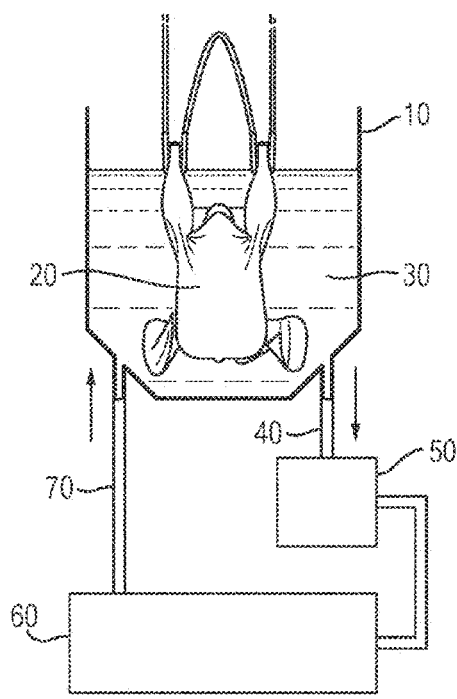
FIG. 10 is a schematic representation showing the application of the electrolysed water solution according to one embodiment of the present invention as a dip or dunk for the in line disinfection of chicken carcasses.

As shown in FIG. 10, the composition of the present invention even at a low dosage provides a >5 log order kill (>99.999%) of *E. coli* elimination on each of the substrates after 20 minutes ($T_2$) of fog exposure. All of the surfaces of the substrates are clear and colourless and no isolated white spots of *E. coli* are visible. FIG. 1D also illustrates that the composition of the present invention provides a >5 log order kill (>99.999%) of *E. coli* elimination on each of the substrates after 40 minutes ($T_3$) of fog exposure.

The present invention provides an electrolyzed water composition having improved efficiency for santizing substrates, including but not limited to wood, steel, plastic and glass substrates.

The present invention provides an electrolyzed water composition providing improved anti-microbial activity, for example improved anti-bacterial activity. Although the present invention demonstrates the effectiveness of the electrolyzed water composition with respect to *E. coli*, it is to be understood that the compositions of the present invention are effective against other microbial strains and are not limited to *E. coli*. elimination. It is also to be understood that the electrolyzed water composition of the present invention may be applied at a higher dosage to the area/substrates and achieve 100% microbial, for example *E. coli*, elimination over a much shorter period of time than achieved for the low dosage application of the composition as shown in this Example. The time for achieving a high microbial kill, such as for example at least 5 log order kill, depends on the concentration of the composition during application. The electrolyzed water compositions of the present invention provide improved antimicrobial activity, for example antibacterial activity, within a significantly shorter time period after exposure to the composition than conventional food-safe disinfecting compositions.

The electrolyzed water composition of the present invention preferably achieves 100% microbial, for example bacterial, elimination within 20 minutes of exposure to the composition. The electrolyzed water composition of the present invention preferably achieves 100% microbial, for example bacterial, elimination within 15 minutes, more preferably within 10 minutes, for example within 5 minutes, of exposure to the composition. The electrolyzed water composition of the present invention preferably achieves at least 80%, more preferably at least 90%, especially preferably at least 95%, for example at least 99.999% (5 log order) microbial, for example bacterial, elimination within 10 minutes, more preferably within 5 minutes, of exposure to the composition by fogging.

Example 4—E. coli Elimination Tests using Flood Based Method

Figure 2A:
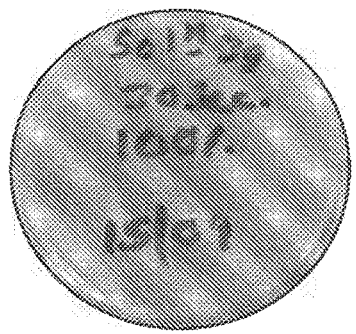
FIGS. 2A to 2C are photographic images illustrating the *E. coli* elimination efficacy of an electrolyzed water composition according to a first embodiment of the present invention applied using a flooding technique as a factor of time after application of the composition.
Figure 2B:
Figure 2C:

Disinfection may also be achieved by flooding the area to be disinfected with the electrolyzed water composition. With reference to FIGS. 2A to 2C, a high concentration (100%) of the electrolyzed water composition of Example 1 was applied to identical substrates contaminated with *E. coli* in FIGS. 2A and 2B. FIG. 2C is a photographic image illustrating the amount of *E. coli* present on the substrate prior ($T_0$) to exposure to the electrolyzed water composition of Example 1. The amount of *E. coli* present on each substrate at time intervals $T_1$ (30 seconds); and $T_2$ (10 minutes) are shown in FIGS. 2A and 2B respectively.

It can be seen by comparing the images of FIGS. 2A and 2B to FIG. 2C that the composition of Example 1 at a concentration of 100% achieved 7 to 8 log order kill (99.999995%) within 30 seconds of application of the composition by a flood based method. The composition of Example 1 applied at a concentration of 100% by flooding therefore achieved a greater log order kill than the composition when applied using the fogging method of Example 3 (5 log order kill).

The compositions of the present invention when applied at a concentration of 100% preferably achieve at least 5 log order kill, more preferably at least 6 log order kill, for example 7 to 8 log order microbial kill within 30 seconds of application of the composition by a flood based method. The compositions of the present invention when applied at a concentration of 100% preferably achieve at least 5 log order kill, preferably at least 6 log order kill, for example 7 to 8 log order microbial kill within 20 seconds of application of the composition by a flood based method. The compositions of the present invention when applied at a concentration of 100% preferably achieve at least 5 log order kill, preferably at least 6 log order kill, for example 7 to 8 log order microbial kill within 10 seconds of application of the composition by a flood based method.

Conventional electrolyzed water compositions based on chloride electrolytes generate free accessible chlorine (FAC). Use of the conventional compositions therefore produces, either when prepared or when reacted, a smell which is associated with swimming pools. There is a risk that disinfected equipment within a food processing environment may produce food products which have become tainted with this chlorine associated smell. In contrast, the electrolyzed water composition of the present invention is substantially free of free accessible chlorine (FAC). In the embodiment used in the example, the composition of Example 1 comprises <0.1 ppm FAC both when produced, and when reacted. The compositions of the present invention may therefore be used to clean and disinfect processing lines and equipment without producing a smell associated with a swimming pool and with a significantly reduced risk of tainting the food product.

The method of disinfecting an area using the compositions of the present invention has significantly reduced environmental issues compared to conventional methods. In contrast to a number of conventional methods, the present invention does not require a considerable water supply and does not produce a large volume of waste water. Furthermore, in accordance with one embodiment of the present invention the electrolyte composition comprises a mixture of sodium chloride, otherwise known as table salt and anhydrous sodium carbonate which is an approved food ingredient (E500) and can be found in, amongst other things, sherbet. In use, the electrolyzed water composition will revert to sodium chloride and sodium carbonate, and neither of these components provides any significant environmental concerns. The other alkali metal carbonate salts, alkali metal chloride salts and/or alkali earth metal chloride salts present within the electrolyte solutions of the present invention are also food safe.

The electrolyzed water composition of the present invention is a food-safe, non-tainting disinfecting composition which can be used to quickly clean and disinfect food processing lines and equipment, in situ, during and/or between shifts, with improved efficiency and with a significantly higher anti-microbial activity than conventional food-safe disinfecting solutions.

Example 5—Salad Washing

In conventional salad washing process, the salad is washed by exposing the salad to up to 60 m³ of chilled (6° C.) water per hour per washing line in order to remove gross debris and reduce the microbial load by 1 log order (90% kill). Approximately half of this water is then removed as waste water every hour.

This conventional process requires a large water supply, produces a significant waste water output and has high energy and cost implications associated with chilling the water supply prior to washing. There are also considerable time constraints associated with this method. It has been found that once the lengthy washing cycles have been completed that there is still a significant microbial presence on the washed salad.

Figure 11:
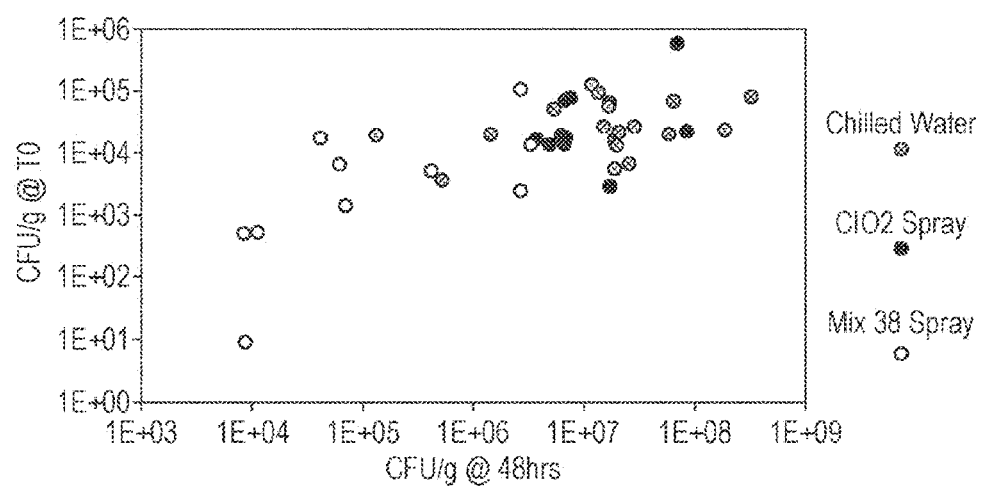
FIG. 11 is a graph showing the reduction in total viable microbial count expressed as Colony Forming Units/gram of food recoverable after washing produce with water; chlorine dioxide treated water; and a solution with the composition of Example 1.

The electrolyzed water composition of Example 1 is sprayed onto the leaves. As shown in FIG. 11, application of the electrolyzed water composition generates a 2.5-3.5 log order kill (99.95%) in 5 second contact time. This represents a significant improvement in antimicrobial activity compared to the conventional salad washing process (90% kill with over 5 minutes contact time).

Furthermore, the methods of the present invention provide electrolyzed water compositions having improved antimicrobial activity which are effective within a significantly shorter time period than the conventional salad washing process. The electrolyzed water composition achieves this level of antimicrobial activity before the salad enters the water washing line.

The composition of the present invention therefore provides a quick and safe method for disinfecting salad which requires a reduced water supply, requires less washing, produces less waste water, has significantly less energy and cost implications and produces a cleaner food product than the conventional salad washing process.

Example 6—Meat Processing

In meat processing plants, a conventional lengthy five-step cutting line clean down procedure is required. This can take a significant amount of time, for example up to 8 hrs per night, in order to clean the equipment sufficiently. The process also involves the use of harsh chemicals and disinfectants and a significant volume of hot water (70° C.). Furthermore, it is difficult to achieve consistent disinfection using conventional methods and as a result potential sources of food cross-contamination may remain. There are therefore environmental and health issues, as well as significant time and cost implications associated with conventional meat processing plant cleaning procedures.

In contrast, the composition of Example 1 is used to disinfect the meat processing plant equipment in a much simplified, for example a 2 stage, process, with improved antimicrobial activity. Furthermore, the composition of Example 1 is used to disinfect the meat processing plant more quickly, for example within a 2 hour time period. The method of the present invention therefore provides quick, effective disinfection of the relevant environment and requires less shutdown time of the processing/preparation equipment. The composition of Example 1 can be used to disinfect the meat processing plant in an automated process using for example a spray bar. Furthermore, the method of the present invention only requires the use of ambient temperature water and therefore there is no need to heat or cool a water supply prior to disinfecting the equipment.

The present invention provides an electrolyzed water composition and a method for disinfecting equipment with improved antimicrobial activity, reduced cost and energy implications, reduced down time of the processing/preparation equipment, and/or reduced environmental implications.

Although Examples 2 to 6 illustrate the effectiveness of the electrolyzed water compositions of the present invention within food processing environments, it is to be understood that the compositions, method and apparatus of the present invention can be used to disinfect any suitable environment, and is not to be limited to food processing environments.

Example 7—Electrolyzed Water Composition

An aqueous electrolyte solution comprising 14 g sodium chloride and 16 g anhydrous sodium carbonate in 12 l of water was prepared. The electrolyte solution was stored within a reservoir chamber in fluid communication with an electrolytic cell.

A feed stream comprising the electrolyte solution was introduced into an electrolytic flow cell. The feed stream can optionally include one or more additional salts to enhance the biocidal properties of the resultant electrolyzed water composition.

The electrolytic cell is a non-membrane electrolytic cell. It is however to be understood that any suitable electrolytic cell may be used.

The electrolytic cell comprises a casing, a plurality of boron doped diamond electrodes (BDEs) located within the cell, and metal 'contact plates' used for transmitting charge across the electrolyte solution.

The BDEs are sheet-like components and are provided in a stack of between 3 and 10 sheets. Each sheet is located at a fixed distance away from an adjacent sheet. The distance between adjacent sheets of BDEs provides a cell gap, which is preferably less than 5 mm, for example between approximately 2 and 3 mm. The BDEs are provided in a plastic frame. The BDEs transmit charge across the electrolyte solution, inducing a strong dipole and creating positively and negatively charged radicals on alternate surfaces of the diamonds.

The electrolyte solution may be introduced into the electrolytic cell in any suitable manner so as to produce electrolyzed water composition in a continuous process or in a batch process. In the continuous process, the electrolyte solution may be introduced at a suitable flow rate, such as for example at a flow rate in the range of from 0.1 to 100 l/min, for example in the range of from 3 to 5 l/min. In the batch process, the electrolyte solution may have a flow rate of approximately 16 l/min.

A power supply was operated to apply a voltage in the range of between 1 and 1,000 Volt D.C. and a current within the range of from 1-1,000 ampere to the electrolyte solution.

The over-potential provided between the electrodes shifts the equilibrium within the electrolyte solution such that a range of 'active species' ions and molecules are produced and remain within the electrolyzed water for a significant amount of time. The term 'significant amount of time' is used herein to refer to at least 10 minutes, preferably at least 30 minutes, more preferably at least 45 minutes, for example at least 60 minutes. The combination of active molecular and ionic species together with the over-potential which supports the equilibrium confers a variable degree of pesticidal activity to the electrolyzed water composition.

The electrolytic cell preferably comprises an outlet through which the electrolyzed water composition exits the cell. The resulting electrolyzed water composition comprises a range of active molecular and ionic species which have biocidal properties.

The active molecular and ionic species include dissolved ozone. The electrolyzed water composition according to this embodiment comprises dissolved ozone at a level of approximately 50 ppm.

Although the electrolyzed water composition of the present invention contains dissolved ozone at a level of approximately 50 ppm, it is to be understood that the electrolyzed water composition of the present invention may comprise any suitable level of dissolved ozone within the range of between 0.1 and 1,000 ppm.

It is also to be understood that the electrolyzed water composition may be varied by varying one or more of: the components of the electrolyte composition, the concentration of the components within the electrolyte composition, the degree of over-potential, the current applied, or any combination thereof. In this way the biocidal properties of the electrolyzed water biocidal composition may be tailored to suit different agricultural targets, such as for example crops, pathogens, delivery mechanism, and time points, or any combination thereof. For example, the biocidal properties of the electrolyzed water biocidal composition may be tailored in relation to when the composition is to be applied, such as for example during preparation of growing beds, during sowing and/or during growing seasons.

The system may further comprise one or more flow regulators arranged in use to adjust the flow of the electrolyte feed stream between the reservoir and the cell.

The system may further comprise a heater arranged in use to adjust the temperature of the flow of the electrolyte feed stream and/or the electrolyte solution within the cell.

The system may further comprise a control system arranged in use to control the flow rate of the electrolyte feed stream as required, such as for example by controlling the flow regulator(s).

The system may comprise a control system arranged in use to control the power supply to the electrodes.

The system may comprise a control system arranged in use to control the temperature of the electrolyte solution.

Control of the temperature of the electrolyte solution, the flow rate of the electrolyte solution feed stream, and the power supply to the electrodes may be provided by a single control system. Alternatively, these factors may be controlled by separate control systems.

Example 8—*Phytophthora infestans* Control on Tomato Plants

*Phytophthora infestans* infected tomato plants were treated with five different treatments.

Treatment 1: untreated control (UT); Treatment 2: Revus (known pesticide);

Treatment 3: Mix 1 (Comparative Example of an alternate electrolysed water solution, with salts comprising NaCl at 0.30 g/l, $Na_2CO_3$ at 1.60 g/l, $KH_2PO_4$ at 0.90 g/l, $KNO_3$ at 0.80 g/l, $CaCl_2.6H_2O$ at 1.60 g/l, $Mg(NO_3)_2.6H_2O$ at 0.80 g/l);

Treatment 4: Mix 60 (Comparative Example of an alternate electrolysed water solution, with salts comprising NaCl at 0.30 g/l, $Na_2CO_3$ at 1.20 g/l, $KH_2PO_4$ at 1.70 g/l, $CaCl_2.6H_2O$ at 1.60 g/l, $Mg(NO_3)_2.6H_2O$ at 1.20 g/l); and Treatment 5: composition of Example 7 (Mix 38).

The treatments were applied using a foliar spray. Each treatment group consisted of four replicates of 8 plants. Each treatment was sprayed onto the diseased plants for 30 seconds. It is to be understood that the treatment is to be applied until the treatment begins to run off from the leaves.

The results of the treatment are illustrated in FIGS. 3A to 3D and FIG. 4.

Figure 3A:
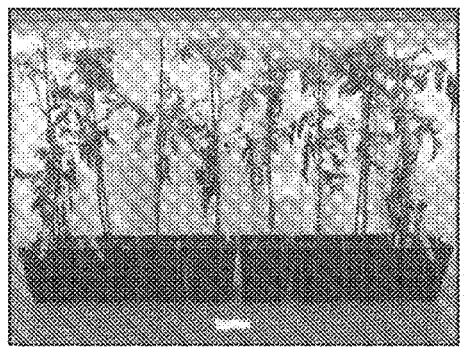
FIGS. 3A and 3B are photographic images illustrating the effect of late blight (*Phytophthora infestans*) on tomato plants when left untreated for ten days (FIG. 3A) and when treated with a conventional treatment agent known as Revus for ten days (FIG. 3B)
Figure 3B:
Figure 3C:
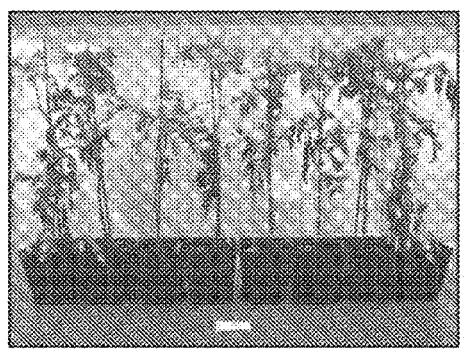
FIGS. 3C and 3D are photographic images illustrating the effect of late blight (*Phytophthora infestans*) on tomato plants when left untreated for ten days (FIG. 3C) and when treated with the Composition of Example 1 for ten days (FIG. 3D)

FIGS. 3A to 3D are photographic images of tomato plants infected with late blight (*Phytophthora infestans*). The tomato plants shown in FIGS. 3A and 3C are not treated with any pesticidal composition (treatment 1). The tomato plants shown in FIG. 3B are treated with a known pesticidal composition known as Revus (treatment 2). The tomato plants shown in FIG. 1D are treated with the composition of Example 7 (treatment 5).

FIGS. 3A and 3C show that the untreated tomato plants are diseased by the plant pathogens. A significant number of the branches and leaves are wilting and diseased.

As shown in FIG. 3B, the tomato plants treated with Revus (treatment 2) appear significantly more healthy than the untreated tomato plants (treatment 1) of FIG. 3A. The tomato plants treated with Revus have less wilting and diseased branches and leaves. This illustrates that Revus is effective at treating at least some of the plant pathogens.

Figure 3D:

As shown in FIG. 3D, the tomato plants treated with the composition of Example 8 (treatment 5) are significantly healthier than the untreated plants of FIGS. 3A and 3C (treatment 1), and healthier than the plants treated with Revus (treatment 2) (FIG. 3B). The tomato plants treated with the composition of Example 8 (treatment 5) appear to have very few wilting or diseased leaves and branches, and ultimately bore 35% more fruit than those treated with Revus.

The electrolyzed water composition of Example 7 therefore has an improved pesticidal effect against late blight than the known pesticide Revus.

Figure 4:
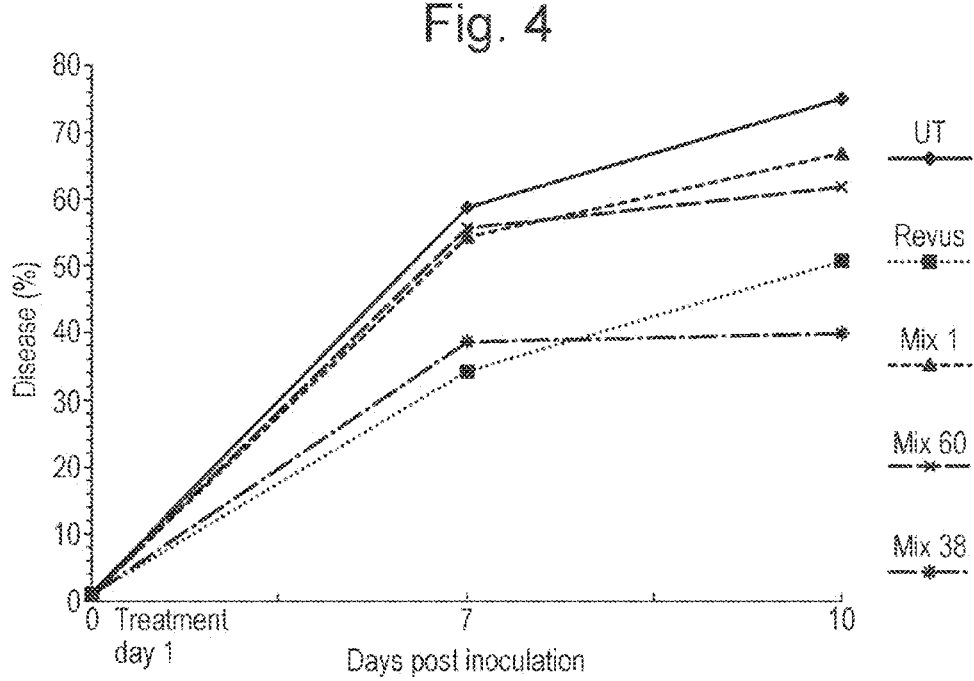
FIG. 4 is a graphical representation comparing the effect of applying the composition of Example 7, and two comparative electrolyzed water compositions; and known pesticide Revus to tomato plants infected with late blight.

FIG. 4 illustrates the degree of crop infection or disease as represented by the percentage of late blight remaining on the tomato plants as a factor of time after treatment. It can be seen that the composition of the present invention (Treatment 5: Composition of Example 7) provides an improved pesticidal effect and significantly reduces the percentage of disease on the plants when compared with the untreated control (treatment 1) and the three other treatments. Treatment 5 (Composition of Example 7) performs better than the known pesticide (Treatment 2).

Example 9—Treatment of Stem *Bortrytis* Infected tomato plants

The average lesion length of diseased plants was measured for five different samples of diseased tomato plants. Each sample was treated with a different treatment regime.

Treatment 1: untreated control (UT);

Treatment 2: known pesticidal agent Signum;

Treatment 3: Mix 1 (Comparative Example of an alternate electrolysed water solution, with salts comprising NaCl at 0.30 g/l, $Na_2CO_3$ at 1.60 g/l, $KH_2PO_4$ at 0.90 g/l, $KNO_3$ at 0.80 g/l, $CaCl_2.6H_2O$ at 1.60 g/l, $Mg(NO_3)_2.6H_2O$ at 0.80 g/l);

Treatment 4: Mix 60 (Comparative Example of an alternate electrolysed water solution, with salts comprising NaCl at 0.30 g/l, $Na_2CO_3$ at 1.20 g/l, $KH_2PO_4$ at 1.70 g/l, $CaCl_2.6H_2O$ at 1.60 g/l, $Mg(NO_3)_2.6H_2O$ at 1.20 g/l); and Treatment 5: composition of Example 7 (Mix 38).

Figure 5:
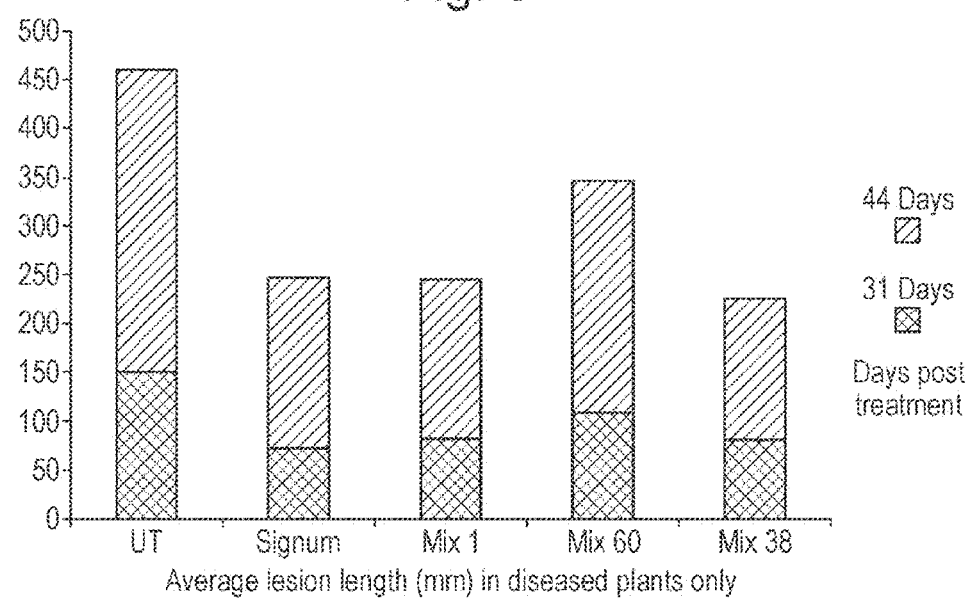
FIG. 5 is a graphical representation comparing the effect of applying the composition of Example 7, two comparative electrolyzed water compositions; and known pesticide Signum on the average lesion length on tomato plants as a factor of number of days post treatment.

The size of the lesions on each plant sample were measured after a period of 31 days and 44 days after treatment. FIG. 5 illustrates the results.

As shown in FIG. 5, it can be seen that each of Treatment 2 to 5 results in a significant reduction in lesion size on each sample of tomato plants. Treatment 3 and Treatment 5 provide a reduction in lesion size which is at least equal to, if not greater, than the reduction provided by the known pesticidal agent, Signum (Treatment 2). Treatment 5 (Composition of Example 7) provides an improved reduction in lesion size present on the sample of plants compared to the known pesticidal agent. Treatment 5 therefore performs better than the known pesticide Signum.

Example 10—Treatment of *Sclerotinia* Infected Carrots

The average disease prevalence in carrot plants was measured for five different samples of plants which had been exposed to the *Sclerotinia* fungus through direct spore transfer. Each sample was identical in the number of carrot plants. The plants were sprayed with a single foliar spray until run off of the treatment solution from the leaves was observed.

Each sample was treated with a different treatment regime.

Treatment 1: untreated control (UT);

Treatment 2: known pesticidal agent Tebecur;

Treatment 3: Mix 1 (Comparative Example of an alternate electrolysed water solution, with salts comprising NaCl at 0.30 g/l, $Na_2CO_3$ at 1.60 g/l, $KH_2PO_4$ at 0.90 g/l, $KNO_3$ at 0.80 g/l, $CaCl_2.6H_2O$ at 1.60 g/l, $Mg(NO_3)_2.6H_2O$ at 0.80 g/l);

Treatment 4: Mix 60 (Comparative Example of an alternate electrolysed water solution, with salts comprising NaCl at 0.30 g/l, $Na_2CO_3$ at 1.20 g/l, $KH_2PO_4$ at 1.70 g/l, $CaCl_2.6H_2O$ at 1.60 g/l, $Mg(NO_3)_2.6H_2O$ at 1.20 g/l); and Treatment 5: composition of Example 7 (Mix 38).

Figure 6:
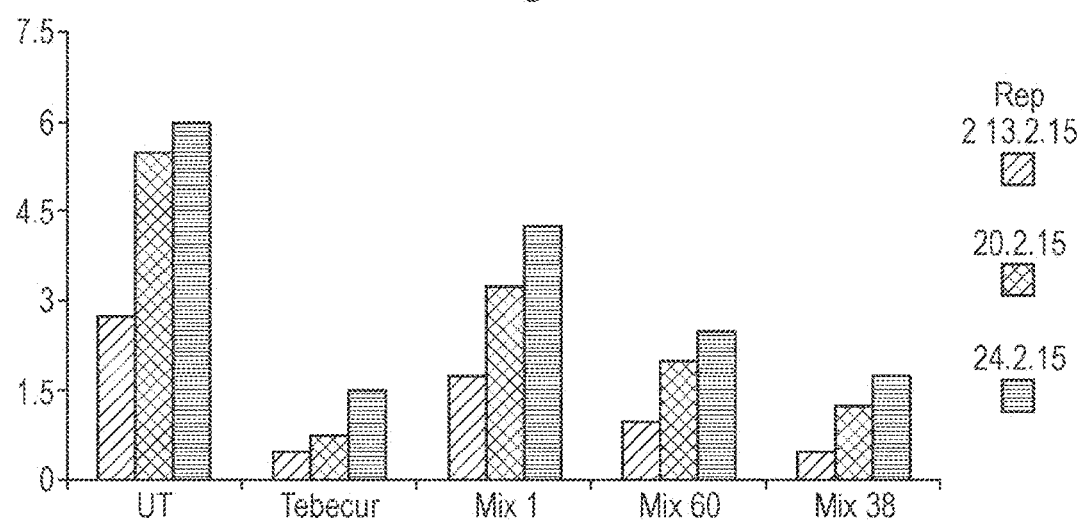
FIG. 6 is a graphical representation comparing the effect of applying the composition of Example 7, two other electrolyzed water compositions as comparative Examples; and known pesticide Tebecur on the average lesion length on carrot plants as a factor of number of days post treatment.

The prevalence of disease in each plant sample was measured after a period of 7 days, 14 days and 21 days after treatment. FIG. 6 illustrates the results.

As shown in FIG. 6, it can be seen that each of Treatment 2 to 5 results in a significant reduction in disease prevalence on each sample of carrot plants at each point of measurement. Treatment 5 (Composition of Example 7) provides an improved reduction in disease prevalence in the sample of plants which is almost equal to the reduction provided by treatment with the known pesticidal agent.

Example 11—Powdery Mildew (*Oidium neolycopersici*) in Tomatoes

Figure 7A:
FIGS. 7A and 7B are photographic images of tomato plants infected with an inoculum of powdery mildew.
Figure 7B:

Groups of tomato plants (of the variety 'Juanita') infected with an inoculum of powdery mildew (as shown in FIGS. 7A and 7B) were treated with six different treatments. Each group consisted of 4 replicates, each having 2 plants per treatment. Each group of tomato plants was sprayed with a single spray of one of the following treatments:

Treatment 1: Untreated;
Treatment 2: Amistar (conventional fungicide);
Treatment 3: Mix 1 (Comparative Example of an alternate electrolysed water solution, with salts comprising NaCl at 0.30 g/l, $Na_2CO_3$ at 1.60 g/l, $KH_2PO_4$ at 0.90 g/l, $KNO_3$ at 0.80 g/l, $CaCl_2.6H_2O$ at 1.60 g/l, $Mg(NO_3)_2.6H_2O$ at 0.80 g/l);
Treatment 4: Mix 60 (Comparative Example of an alternate electrolysed water solution, with salts comprising NaCl at 0.30 g/l, $Na_2CO_3$ at 1.20 g/l, $KH_2PO_4$ at 1.70 g/l, $CaCl_2.6H_2O$ at 1.60 g/l, $Mg(NO_3)_2.6H_2O$ at 1.20 g/l);
Treatment 5: Composition of Example 7 comprising sodium salts; and
Treatment 6: Composition of the present invention (K38) comprising potassium carbonate and potassium chloride in the same carbonate: chloride ratio by weight as the composition of Example 7; and The plants were stored in a NIAB growth room using daily conditions cycle of 20° C. for a 16 hour day, and then 16° C. for an 8 hour night.

Figure 8:
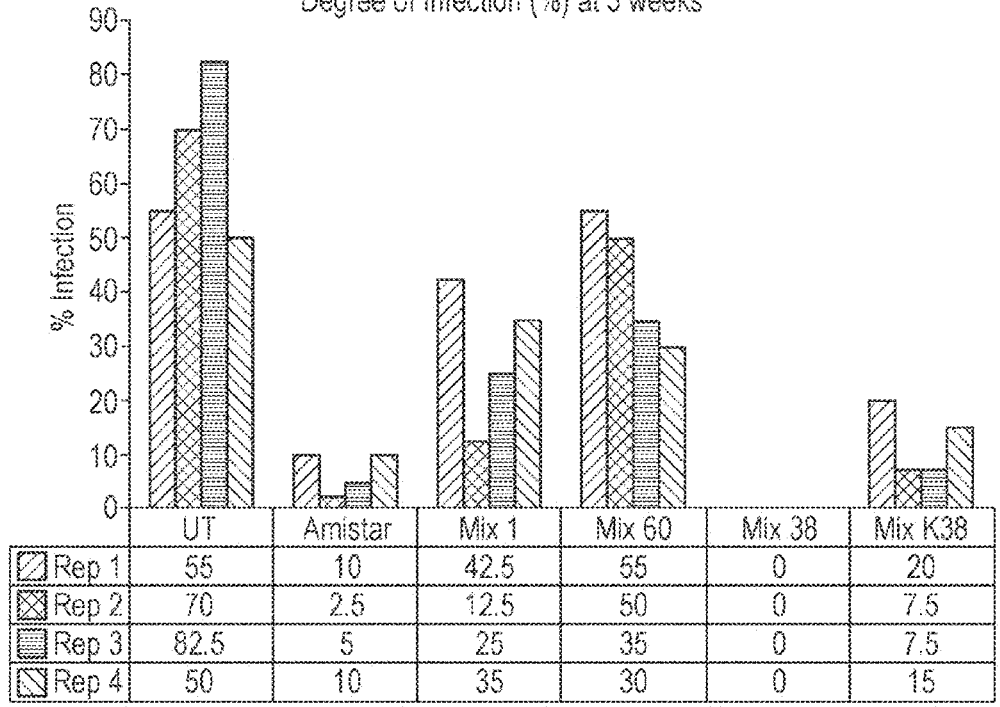
FIG. 8 is a graphical representation comparing the degree of infection (%) of powdery mildew infected tomato plants 3 weeks after treatment with the composition of Example 7, three comparative electrolyzed water compositions, Amistar (a known fungicide), and without treatment.

The plants were then scored for the degree of infection 3 weeks after the single spray treatment. The results are illustrated in FIG. 8. As can be seen from FIG. 8, the conventional fungicide (Amistar) provided good control of the infection. However, it can also be seen that the Composition of Example 7 provided plants having no visible signs of infection. The composition of Example 7 therefore provided an improved fungicidal effect compared to the known fungicide.

Each of the comparative Examples (Treatments 3 and 4) provided a degree of fungicidal activity. However, none of the comparative Examples provided a fungicidal effect which was as effective as either the known fungicide, Amistar or the Composition of Example 7.

Figure 9:
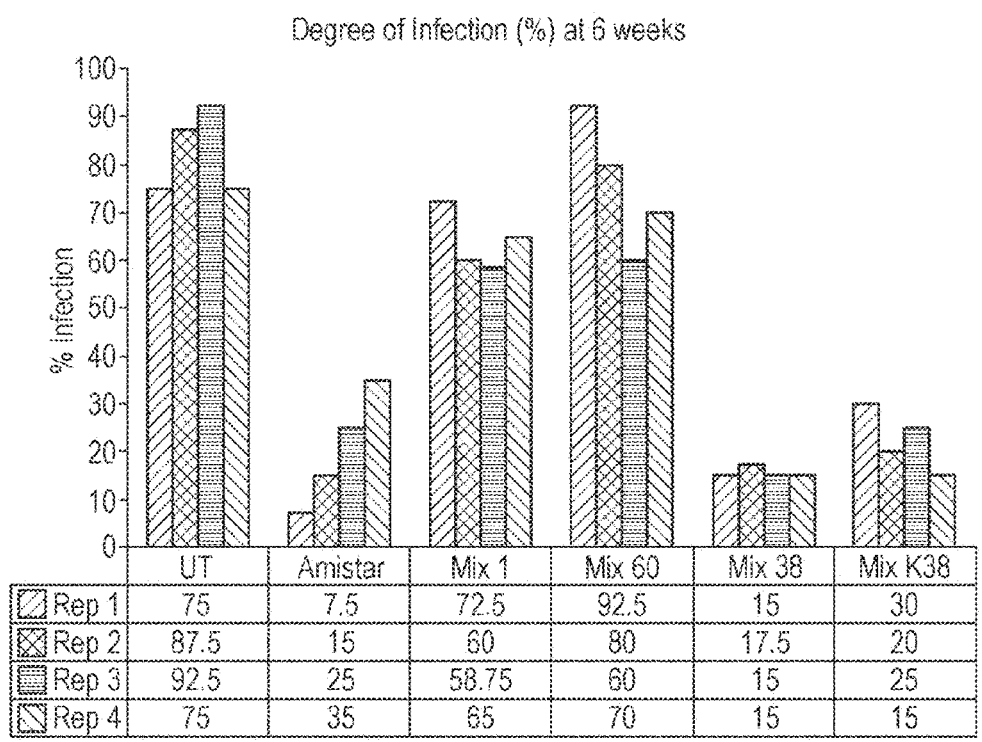
FIG. 9 is a graphical representation comparing the degree of infection (%) of powdery mildew infected tomato plants 6 weeks after treatment with the composition of Example 7, three comparative electrolyzed water compositions, Amistar (a known fungicide), and without treatment.

The plants were left for a further three weeks (a total of 6 weeks after single spray treatment) without any further treatment. The plants were then scored again for the degree of infection 6 weeks after the single spray treatment. The results are illustrated in FIG. 9. As can be seen from FIGS. 8 and 9, the Composition of Example 1 provides a significant medium-term protective effect (FIG. 8) and an ongoing protective effect (FIG. 9) which has lasted for at least 6 weeks. The compositions of the present invention are believed to cause a Systemic Acquired Response inductive effect within the tomato plants.

The method of pesticidal treatment of a substrate using the compositions of the present invention have significantly reduced environmental issues compared to conventional methods. In contrast to a number of conventional methods, the compositions of the present invention contain only simple, non-toxic and food-approved salts. The compositions of the present invention are therefore more environmentally friendly than known pesticidal compositions. Furthermore, the compositions of the present invention do not leave any harmful chemical residues on treated food. The compositions of the present invention are non-toxic and non-tainting. The compositions of the present invention have a significantly improved ozone concentration compared to the level which can be achieved by injection of gaseous ozone into water. For example, the compositions of the present invention may have approximately 100 times the level which can be achieved by injection of gaseous ozone into water. As such, the compositions of the present invention may be used more frequently, during extended periods of crop production, such as for example closer to crop harvest, and without requiring any additional health and safety protection or equipment. The compositions of the present invention provide a cost effective alternative to the use of known chemical pesticides. The compositions of the present invention provide medium term protective effect and an ongoing protective effect.

It is to be understood that Examples 7 to 11 are illustrative of the pesticidal properties of the compositions of the present invention. It is to be understood that the compositions of the present invention may be applied in any suitable manner to an agricultural area or crop(s).

Although the Examples 7 to 11 illustrate the use of the compositions of the present invention for the treatment of crops, it is to be understood that the compositions of the present invention may be used for the treatment of soil, and/or in any suitable industry, in particular the agricultural industry, which requires the use of pesticidal compositions. For example, the compositions of the present invention may be used to treat any equipment, such as for example irrigation systems, tanks including water tanks, and/or crop treatment equipment as well as water such as for example surface, rain and/or ground water.

Example 12—Electrolyzed Water Composition

An electrolyte solution comprising a total salt concentration of 10.4 g/l in water (5.6 g/l anhydrous sodium carbonate ($Na_2CO_3$) and 4.8 g/l sodium chloride (NaCl)) was prepared. The electrolyte solution is stored within a reservoir chamber in fluid communication with an electrolytic cell.

A feed stream comprising the electrolyte solution was introduced into the electrolytic cell. The feed stream can optionally include one or more additional salts to enhance the antipathogenic properties of the resultant electrolyzed water composition. The electrolytic cell is a non-membrane electrolytic cell. The electrolytic cell comprises a casing, a plurality of boron doped diamond electrodes (BDEs) located within the cell, and metal 'contact plates' used for transmitting charge across the electrolyte solution.

The BDEs are sheet-like components and are provided in a stack of between 3 and 10 sheets. Each sheet is located at a fixed distance away from an adjacent sheet. The distance between adjacent sheets of BDEs provides a cell gap, which is preferably less than 5 mm, for example between approximately 2 and 3 mm. The BDEs are provided in a plastic frame. The BDEs transmit charge across the electrolyte solution, inducing a strong dipole and creating positively and negatively charged radicals on alternate surfaces of the diamonds.

The electrolyte solution may be introduced into the electrolytic cell in any suitable manner so as to produce electrolyzed water composition in a continuous process or in a batch process. In the continuous process, the electrolyte solution may be introduced at a suitable flow rate, such as for example at a flow rate in the range of from 0.1 to 100 l/min, for example in the range of from 3 to 5 l/min. In the batch process, the electrolyte solution may have a flow rate of approximately 16 l/min.

A power supply was operated to apply a voltage in the range of between 1 and 1000 Volt D.C. and a current within the range of from 1-1000 ampere to the electrolyte solution. The over-potential provided between the electrodes shifts the equilibrium within the electrolyte solution such that dissolved ozone is produced and remains within the electrolyzed water for a significant amount of time. For example, the half life of the dissolved ozone within the electrolyzed water composition is preferably at least a number of minutes, more preferably at least ten minutes, especially preferably at least 30 minutes, for example about 45 minutes.

The electrolytic cell preferably comprises an outlet through which the electrolyzed water composition exits the cell. The electrolyzed water composition preferably also has detergent properties. The electrolyzed water composition preferably comprises surfactant species.

The electrolyzed water composition according to this embodiment comprises dissolved ozone at a level of approximately 300 ppm. This level of dissolved ozone is approximately 100 times greater than the level which can be achieved by injecting gaseous ozone into water. As a result, the electrolyzed water composition of the present invention has an increased anti-microbial efficacy compared to water which has been injected with gaseous ozone. The electrolyzed water composition may be used as an antipathogenic agent against food borne pathogens.

Although the electrolyzed water composition of the present invention contains dissolved ozone at a level of approximately 300 ppm, it is to be understood that the electrolyzed water composition of the present invention may comprise any suitable level of dissolved ozone, preferably within the range of between 0.1 and 10000 ppm, preferably between 1 and 1000 ppm.

Conventional electrolyzed water compositions based on chloride electrolytes generate free accessible chlorine (FAC). Use of the conventional compositions therefore produces, either when prepared or when reacted, a smell which is associated with swimming pools. There is a risk that disinfected equipment within a food processing environment may produce food products which have become tainted with this chlorine associated smell. In contrast, the electrolyzed water composition of the present invention is substantially free of free accessible chlorine (FAC). In the embodiment used in the example, the composition of Example 1 comprises <0.1 ppm FAC both when produced, and when reacted. The compositions of the present invention may therefore be used to clean and disinfect processing lines and equipment without producing a smell associated with a swimming pool and with a significantly reduced risk of tainting the food product.

Example 13

With reference to Tables 2 and 3, three groups of 30 poultry carcasses were treated with three different treatment methods.

Treatment 1: Untreated as a control sample;

Treatment 2: the Sonosteam process involving exposure to steam and ultrasound.

Treatment 3: the Sonosteam process followed by exposure to the electrolyzed water composition of Example 12. The Sonosteam treated poultry carcasses were immersed for 20 seconds per bird in a reservoir comprising the electrolyzed water composition of Example 12 as shown in FIG. 10. The chicken carcass 20 is dunked into a bath 10 containing a circulating solution 30 of the electrolyzed water composition of Example 12. The solution is circulated by means of a pump 50 which draws solution from through a pipe 40 from the end of the bath, filters it and passes it for re-electrolysis and heating in the BDE flow cell 60. The re-electrolyzed solution is returned to the start of the bath by means of a pipe 70. The electrolyzed water composition of Example 13 was warmed to and maintained at a temperature between 40° C. and 46° C.

The poultry carcasses of each group were then subjected to biopsy of the neck skin (a particularly difficult area to treat effectively) and breast skin (an easier part of the carcass to treat), with weighed skin samples being sent to a specialist testing lab to determine the level of Campylobacter present (as colony forming units/gram of skin) at the day of kill (herein referred to as DOK) plus 4 days (Table 2); and again at the day of kill plus 7 days (Table 3).

TABLE 2

Campylobacter level at DOK plus 4 days

| Treatment | Campylobacter Level ($\log_{10}$) | Birds > 1,000 cfu/g |
|---|---|---|
| Treatment 1 (Control) | 3.10 | 35% |
| Treatment 2 (Sonosteam) | 2.85 | 30% |
| Treatment 3 (Sonosteam + Composition of Example 12) | 1.70 | 0% |

The average background contamination level of Campylobacter after 4 days (DOK plus 4 days) was found to be 3+ log (ie. 1000 cfu/g). 35% of the group of the untreated control poultry carcasses were found, after four days, to have a level of Campylobacter of greater than 1000 cfu/g. This level of Campylobacter contamination is considered to be indicative of a heavily contaminated group of poultry.

TABLE 3

Campylobacter level at DOK plus 7 days

| Treatment | Campylobacter Level ($\log_{10}$) | Birds > 1,000 cfu/g |
|---|---|---|
| Treatment 1 (Control) | 2.66 | 30% |
| Treatment 2 (Sonosteam) | 2.30 | 14% |
| Treatment 3 (Sonosteam + Composition of Example 12) | 1.27 | 0% |

As shown in Tables 2 and 3, exposure of the carcass to the composition of Example 13 for a time period of 20 seconds per bird results in a reduction in the level of Campylobacter of at least 1 log (90%). The level of reduction may be further improved by prolonged exposure to the composition of Example 12. This significant reduction in the level of Campylobacter furthermore would result in a significant reduction in the number of human food poisonings as a result of eating contaminated poultry carcasses. This significant reduction in the level of Campylobacter would therefore have significant benefits and associated cost savings for food producers, such as for example poultry farmers, food processors, and retailers.

It can be seen from Tables 2 and 3 that the electrolyzed water compositions of the present invention achieves a significant reduction of at least 95% of Campylobacter pathogens on the poultry carcasses over a period of at least 7 days from the Day of Kill. Furthermore, the compositions of the present invention are effective in ensuring that no carcasses within the group have a *Campylobacter* level of over 1000 cfu/g. The compositions of the present invention are therefore effective in reducing pathogen levels on carcasses to be within safer limits and thereby significantly reducing the risk of food poisoning.

The compositions of the present invention have also been found to not provide any negative organoleptic results, such as for example poor taste or smell residues and/or visual or tactile degradation of carcass quality.

The present invention provides an electrolyzed water composition providing improved anti-pathogenic activity on or in food substrates. Although the present invention demonstrates the effectiveness of the electrolyzed water composition with respect to reducing and/or *Campylobacter* on poultry carcasses, it is to be understood that the compositions of the present invention are effective against other pathogens, and in particular food borne pathogens, and are not limited to *Campylobacter* reduction and/or elimination. The compositions of the present invention are effective against a number of different pathogens on any suitable food substrate and are therefore not limited to reduction and/or eliminated of pathogens on or in poultry carcasses. The compositions of the present invention may be applied to the food substrate by any suitable method and/or for any suitable application time.

It is also to be understood that the electrolyzed water compositions of the present invention may be applied at a higher dosage to the food substrate, and/or may reduce and/or eliminate food borne pathogens over a much shorter period of time than achieved for the low dosage application of the composition as shown in this Example.

Example 14

With reference to Table 4, three groups of 30 poultry carcasses were treated with three different treatment methods.

Treatment 1: Untreated as a control sample;
Treatment 2: the Sonosteam process involving exposure to steam and ultrasound.
Treatment 3: exposure to the electrolyzed water composition of Example 12. The poultry carcasses were immersed for 15 seconds per bird in a reservoir comprising the electrolyzed water composition of Example 12. The electrolyzed water composition of Example 12 was warmed to and maintained at a temperature between 43° C. and 50° C.

The poultry carcasses of each group were then subjected to biopsy of the neck skin and breast skin, with weighed skin samples being sent to a specialist testing lab to determine the level of *Campylobacter* present at day of kill plus 4 days (Table 4).

TABLE 4

*Campylobacter* level at DOK plus 4 days

| Treatment | *Campylobacter* Level ($\log_{10}$) | Birds > 1,000 cfu/g |
|---|---|---|
| Treatment 1 (Control) | 2.01 | 7% |
| Treatment 2 (Sonosteam) | 1.47 | 0% |
| Treatment 3 (Composition of Example 12) | 1.17 | 0% |

The average background contamination level of *Campylobacter* after 4 days (DOK plus 4 days) was found to be 2+ log (ie. 100 cfu/g). 7% of the group of the untreated control poultry carcasses were found, after four days, to have a level of *Campylobacter* of greater than 1000 cfu/g. This level of *Campylobacter* contamination is considered to be indicative of an unusually lowly contaminated group of poultry, and smaller level of reductions following treatment are expected when the starting population of *Campylobacter* is lower.

Although Examples 12 to 14 illustrate the effectiveness of embodiments of the electrolyzed water compositions of the present invention within poultry processing environments, it is to be understood that the compositions, method and apparatus of the present invention can be used to reduce and/or eliminate food borne pathogens in any suitable environment, and is not to be limited to poultry processing environments.

The invention claimed is:

1. A method for producing an electrolyzed water composition that is devoid of free accessible chlorine (FAC), the method comprising:
   preparing a starting electrolyte solution comprising water, at least one carbonate salt selected from: anhydrous alkali metal carbonate salts, and at least one chloride salt selected from: alkali metal chloride salts and/or alkali earth metal chloride salts, in which the total salt concentration of carbonate salts and chloride salts in the electrolyte solution is in the range of between 5 g/l and 50 g/l, and in which the ratio of the carbonate salts to chloride salts by weight within the electrolyte solution is in the range of between 0.5:1 to about 2.0:1;
   introducing the starting electrolyte solution into the chamber of an electrolytic cell comprising a plurality of boron-doped diamond electrodes and metal contact plates;
   operating a power supply to apply a predetermined voltage to the starting electrolyte solution within the electrolytic cell; and
   producing an electrolyzed water composition that is FAC-free and comprises a plurality of active molecular and ionic species selected from the group consisting of ozone, hydrogen peroxide, hydroxyl ions and hydronium ions.

2. A method as claimed in claim 1, in which the mixture of the at least one chloride salt and the at least one carbonate salt are selected to produce an ozone concentration in the range of from 0.1 to 1,000 ppm.

3. A method as claimed in claim 1, in which the starting electrolyte solution is introduced into the electrolytic cell in a continuous or batch process manner.

4. A method as claimed in claim 1, in which the predetermined voltage is in the range of between about 1 and 1000 volts DC.

5. A method as claimed in claim 1, in which the power supply has a current in the range of between about 1 and 1000 ampere.

6. An electrolyzed water composition obtainable by a method as claimed in claim 1.

7. An electrolyzed water composition as claimed in claim 6, in which the composition has antimicrobial properties and is substantially chlorine-free.

8. An electrolyzed water composition as claimed in claim 6, in which the composition is used as an antimicrobial agent, or an antibacterial agent, or as a cleaning agent, or as a pesticidal agent, or for reducing and/or eliminating food borne pathogens on or in a food substrate.

* * * * *